(12) United States Patent
Jeannin et al.

(10) Patent No.: US 6,358,988 B1
(45) Date of Patent: Mar. 19, 2002

(54) PROCESS AND COMPOSITION FOR THE ANTIPARASITIC TREATMENT OF THE SURROUNDINGS OF ANIMALS

(75) Inventors: Philippe Jeannin, Tournefeuille (FR); James William Smith; Samuel Perry Yenne, both of Raleigh, NC (US)

(73) Assignee: Merial, Lyons (FR)

( * ) Notice: Subject to any disclaimer, the term of this patent is extended or adjusted under 35 U.S.C. 154(b) by 0 days.

(21) Appl. No.: 09/230,283

(22) PCT Filed: Jul. 17, 1997

(86) PCT No.: PCT/EP97/03829

§ 371 Date: Apr. 23, 1999

§ 102(e) Date: Apr. 23, 1999

(87) PCT Pub. No.: WO98/03071

PCT Pub. Date: Jan. 29, 1998

Related U.S. Application Data

(60) Provisional application No. 60/022,059, filed on Jul. 23, 1996.

(51) Int. Cl.$^7$ .............................................. H01N 43/56

(52) U.S. Cl. ........................ 514/404; 514/406; 514/407

(58) Field of Search ................................ 514/404, 406, 514/407

(56) References Cited

U.S. PATENT DOCUMENTS

| | | | |
|---|---|---|---|
| 5,232,940 A | 8/1993 | Hatton et al. | 514/407 |
| 5,236,938 A | 8/1993 | Huang et al. | 514/341 |

FOREIGN PATENT DOCUMENTS

| | | |
|---|---|---|
| DE | 19511269 | 10/1995 |
| EP | 0295117 | 12/1988 |
| EP | 0385809 | 9/1990 |
| EP | 0403300 | 12/1990 |
| EP | 0500209 | 8/1992 |
| EP | 0679650 | 11/1995 |
| WO | 87/03781 | 7/1987 |
| WO | 93/06089 | 4/1993 |
| WO | 94/21606 | 9/1994 |
| WO | 96/16544 | 6/1999 |

OTHER PUBLICATIONS

Database CROUPU, STN–International, STN–accession No. 90–82077 (1990).
Database CROUPU, STN–International, STN–accession No. 87–87287 (1987).
Database Medline, STN–International No. 97–155922 (1997).

*Primary Examiner*—Allen J. Robinson
(74) *Attorney, Agent, or Firm*—Burns, Doane, Swecker & Mathis, L.L.P.

(57) ABSTRACT

Processes for the antiparasitic control of darkling beetles utilizing 1-arylpyrazole insecticides and for applying said insecticides to animal litter, especially for animal rearing, are described. Also described are mixtures of carbaryl and 1-arylpyrazole insecticides.

31 Claims, No Drawings

PROCESS AND COMPOSITION FOR THE ANTIPARASITIC TREATMENT OF THE SURROUNDINGS OF ANIMALS

This application is the U.S. national phase of International Patent Application No PCT/EP97/03829, filed Jul. 17, 1997 and designating the United States, incorporated by reference herein in its entirety and relied upon, which in turn claims the priority of U.S. Provisional Application No. 60/022,059, filed Jul. 23, 1996.

The present invention relates to a process for the antiparasitic treatment of the surroundings of animals, in particular of animal litter and of rearing buildings, in particular for the purpose of protecting them against parasites from the darkling beetle family.

In the present text, animal litter is taken in the broad sense, that is to say that this term comprises beds made of plant or other material on which the animals lie or gather, including open-air sites or places, in particular those of the "feed lot" type in North America.

The invention also encompasses the treatment of liquid manure, in particular in the vicinity of animal rearing sites. The invention applies to the litter and liquid manure of all types of animals but is very particularly applied in the avian field (in particular chickens, turkeys, guinea fowls, ducks, geese and laying hens).

The invention also applies to ready-to-use litter or to litter components treated by the process according to the invention.

The intensive rearing of animals intended for consumption results in a large number of animals being confined in a restricted space. This applies both to small animals, such as poultry and rabbits and others, and to large animals, such as cattle, pigs and the like.

Broilers are, for example, reared for 8 weeks on average. Between two groups, that is to say between two rearing cycles, the breeder generally cleans the site, with the site being left empty for several days for health reasons.

However, the frequency at which breeders clean the rearing area and more particularly the litter is always limited by rearing requirements. Animal rearing sites are therefore centres for the development of parasites in the general sense, including insects. This naturally has a direct impact on the sanitary condition of the sites and on the health of the animals and indirectly on rearing productivity.

Poultry litter is basically composed of materials of plant origin, such as, for example, sawdust or wood chippings, with which dejecta or excrement from the animals will be mixed in time. As the litter is not changed at each rearing cycle, the thickness of the soiled litter frequently reaches several tens of centimeter. In particular, beetles from the Tenebrionidae family, also known as darkling beetles, develop therein. The treatment of poultry litter is a problem which is particularly difficult to solve in that any product used to treat this litter has a tendency to be absorbed by the litter, either by the excrement which is found therein or by the plant matter which is found therein. Moreover, the continuous arrival of fresh excrement tends to isolate the insecticidal materials from the site to be treated.

Darkling beetles comprise various species. One of the main species is *Alphitobius diaperinus*; this species is particularly well controlled by the present invention. Another darkling beetle species is *Tenebrio molitor*. Another species of parasite which infests poultry litter is *Dermestes maculatus*.

The presence of these parasites, especially darkling beetles, has two impacts with serious economic consequences.

The first impact is on the growth of the poultry. In poultry rearing, the speed of the rearing cycle is an economically determining factor and the least disturbance to food intake has consequences for the growth of the animals. Now, these beetles are ingested by poultry, and particularly by chicks, and they can then cause slow-down in growth.

The second impact is on the very structure of the rearing buildings. In fact, at the adult stage, in particular between two rearing cycles, the adult beetles can ascend into the structures of the buildings and lay their eggs there. The larvae, before redescending into the litter, have a tendency to devour the heat-insulation materials, such as polystyrene. Now, poultry is very sensitive to the temperature, so that the consequences of such a deterioration can be catastrophic with respect to the progression of the rearing. The rearing buildings must therefore frequently be repaired or replaced.

Laying hens and rabbits are both raised on gratings and their dejecta or excrement are continuously discharged and generally stored in the vicinity of the rearing buildings. The liquid manure which thus accumulates itself also exhibits the disadvantages cited above with respect to the sanitary condition of the sites and the health of the animals.

Another problem frequently encountered is the presence of flies, in particular the house fly, the larvae of which develop within the soiled litter and the liquid manure. These flies are a nuisance both to animals and to man, in and in the vicinity of the animal rearing site. In addition, these flies can be the vector for infectious agents and can be responsible for epidemic pathologies.

Darkling beetles are insects/parasites which are particularly difficult to remove. This difficulty is illustrated by the fact that there is only a single product which has been successful commercially: this is the product known under the name of carbaryl [1-naphthyl methylcarbamate]. This is all the more surprising since this product is an old product, being at least forty years old and although a number of insecticides have been developed since, none has been in a position to supplant carbaryl with respect to poultry. Unfortunately, carbaryl is a product which, in a number of respects, has a limited performance, both as regards effectiveness and as regards the duration of this effectiveness. An explanation for this currently existing lack of worthwhile products probably results from the difficulty of treating animal litter, as has been explained above.

A first object of the invention is to provide a process and compositions which can completely or partially solve the problems indicated above.

Another object of the invention is to provide means for combating darkling beetles or insects from the Tenebrionidae family, especially *Alphitobius diaperinus*.

Another object of the invention is to provide means for combating parasitic insects commonly found in animal litter and known under the name of *Dermestes maculatus* or under the name of insects from the Tenebrionidae family, such as *Alphitobius diaperinus* and *Tenebrio molitor*.

Another object of the present invention is to provide a process for the antiparasitic treatment of floors, litter or liquid manure which is particularly effective against darkling beetles and flies, while being easy and practical to use in commercial rearing, especially poultry rearing.

Another object of the present invention is to provide a process for the antiparasitic treatment of sites where poultry lives or should live, the said sites being infested or capable of being infested by darkling beetles.

Yet another objective of the invention is to provide a process which only requires treatments at widely spaced intervals and even, in particular in the case of the rearing of broilers, which only requires a single treatment per rearing cycle, before installing the young animals.

Yet another objective of the invention is to provide a process suitable for the preparation of litter components or of ready-to-use litter which have been treated against these parasites, in particular for the whole of their period of use.

These objects are met in whole or in part by the present invention.

A subject of the present invention is therefore a process for the antiparasitic treatment of sites infested or capable of being infested by darkling beetles, in which an effective amount of a composition comprising at least one compound corresponding to the formula (I) defined below is applied to the said site.

According to another aspect, a subject of the present invention is a process for the antiparasitic treatment of sites infested or capable of being infested by darkling beetles, in which an effective amount of a composition comprising at least one compound corresponding to the formula (I) is applied to the said site. The said sites comprising floors, litter, liquid manure or the like.

According to another aspect, a subject of the present invention is a process for the antiparasitic treatment of rearing places or buildings, in particular for commercial rearing, in particular of poultry, and more especially of sites infested or capable of being infested by darkling beetles, the said process comprising the application to the said site of an effective amount of a composition comprising at least one compound corresponding to the formula (I).

According to another aspect, the invention relates to a means for combating darkling beetles or insects from the Tenebrionidae family, especially *Alphitobius diaperinus*, the said process comprising the application to the sites infested or capable of being infested by the said darkling beetles of an effective amount of a composition comprising at least one compound corresponding to the formula (I).

Another object of the invention is to provide means for combating the insects known under the name of *Dermestes maculatus*, the said process comprising the application to the sites (floors, litter, liquid manure, places or buildings) of an effective amount of a composition comprising at least one compound corresponding to the formula (I).

The present invention further relates to a process for the antiparasitic treatment of the surroundings of animals, in particular of sites infested or capable of being infested by a parasite from the group composed of a darkling beetle and/or *Alphitobius diaperinus* and/or *Dermestes maculatus* and/or *Tenebrio molitor*, the said treatment comprising the application to the said surroundings or to the said site of an effective amount of a composition comprising at least one compound corresponding to the formula (I). According to one aspect of this invention, these infested sites or sites capable of being infested are floors, litter or liquid manure or the like. According to another aspect, these sites are commercial rearing places or buildings.

The present invention therefore further relates to a process for the antiparasitic treatment of sites infested or capable of being infested by an insect from the group composed of darkling beetles and/or *Alphitobius diaperinus* and/or *Dermestes maculatus* and/or *Tenebrio molitor*, in which an effective amount of a composition comprising at least one compound corresponding to the formula (I) is applied to the said site, the said process being carried out at a frequency of less than once per month.

The present invention therefore further relates to a process for the antiparasitic treatment of sites infested or capable of being infested by an insect from the group composed of darkling beetles and/or *Alphitobius diaperinus* and/or *Dermestes maculatus* and/or *Tenebrio molitor*, in which an effective amount of a composition comprising at least one compound corresponding to the formula (I) is applied to the said site, the said process being carried out at a frequency not exceeding once per rearing cycle.

The products of formula (I) used in the invention are products, the formula of which is:

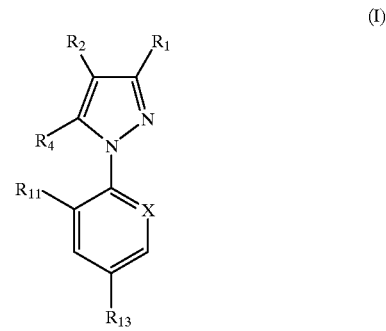

(I)

in which:

R$_1$ is a halogen atom or a CN or methyl group;

R$_2$ is S(O)$_n$R$_3$ or 4,5-dicyanoimidazol-2-yl or haloalkyl;

R$_3$ is alkyl or haloalkyl;

R$_4$ represents a hydrogen or halogen atom; or an NR$_5$R$_6$, S(O)$_m$R$_7$, C(O)R$_7$ or C(O)O—R$_7$, alkyl, haloalkyl or OR$_8$ radical or an —N=C(R$_9$)(R$_{10}$) radical;

R$_5$ and R$_6$ independently represent a hydrogen atom or an alkyl, haloalkyl, C(O)alkyl, alkoxycarbonyl, S(O)$_r$CF$_3$ radical; or R$_5$ and R$_6$ can together form a divalent alkylene radical which can be interrupted by one or two divalent heteroatoms, such as oxygen or sulphur;

R$_7$ represents an alkyl or haloalkyl radical;

R$_8$ represents an alkyl or haloalkyl radical or a hydrogen atom;

R$_9$ represents an alkyl radical or a hydrogen atom;

R$_{10}$ represents a phenyl or heteroaryl group optionally substituted by one or a number of halogen atoms or groups such as OH, —O-alkyl, —S-alkyl, cyano or alkyl;

R$_{11}$ and R$_{12}$ represent independently of one another, a hydrogen or halogen atom and optionally CN or NO$_2$ but H or halogen are preferred;

R$_{13}$ represents a halogen atom or a haloalkyl, haloalkoxy, S(O)$_q$CF$_3$ or SF$_5$ group;

m, n, q and r represent, independently of one another, an integer equal to 0, 1 or 2;

X represents a trivalent nitrogen atom or a C—R$_{12}$ radical, the other three valencies of the carbon atom forming part of the aromatic ring;

with the proviso that, when R$_1$ is methyl, then either R$_3$ is haloalkyl, R$_4$ is NH$_2$, R$_{11}$ is Cl, R$_{13}$ is CF$_3$ and X is N; or else R$_2$ is 4,5-dicyanoimidazol-2-yl, R$_4$ is Cl, R$_{11}$ is Cl, R$_{13}$ is CF$_3$ and X is =C—Cl.

The alkyl radicals of the definition of the formula (I) generally comprise from 1 to 6 carbon atoms. The ring formed by the divalent alkylene radical representing R$_5$ and R$_6$ and by the nitrogen atom to which R$_5$ and R$_6$ are attached is generally a 5-, 6- or 7-membered ring.

A preferred class of compounds of the formula (I) comprises the compounds such that R$_1$ is CN and/or R$_3$ is haloalkyl and/or R$_4$ is NH$_2$ and/or X is CR$_{12}$ and/or R$_{11}$ and $R_{12}$ are, independently of one another, a halogen atom and/or $R_{13}$ is haloalkyl.

A compound of formula (I) which is very particularly preferred in the invention is 1-[2,6-$Cl_2$-4-$CF_3$phenyl]-3-CN-4-[SO—$CF_3$]-5-$NH_2$pyrazole, hereinafter known as compound A.

Compounds of formula (I) can be prepared according to one or other of the processes described in Patent Applications WO 87/3781, 93/6089 or 94/21606 or European Patent Applications 295,117, 403,300, 385,809 or 679,650 or German Patent Application 19511269 or in U.S. Pat. Nos. 5,232,940 and 5,236,938 or any other process coming within the competence of the person skilled in the art who is an expert in chemical synthesis. For the chemical preparation of the products of the invention, the person skilled in the art is regarded as having available, inter alia, all the contents of "Chemical Abstracts" and of the documents which are cited therein. Compositions comprising the compounds of formula (I) can also be prepared according to the teaching of this same prior art or of a similar prior art.

According to another aspect of the present invention, the latter relates to pesticidal compositions intended to be used in the processes defined above. These pesticidal compositions comprise at least one active compound of formula (I) mixed with solid or liquid vehicles and/or surface-active agents, these various constituents being acceptable in agriculture and/or in aviculture and/or in the veterinary field and/or, preferably, in the field of animal rearing. In particular, the inert and conventional vehicles and the conventional surface-active agents can be used.

The compositions used in the invention can either be compositions, generally diluted, which are ready to be applied to the site infested or capable of being infested by the parasite or can be concentrated compositions (better suited to commercialization or storage), which have to be diluted before application. The dilute composition can be prepared either by diluting with water from a commercial concentrated composition containing the active material (the concentrated mixture being called "ready mix") or by means of the mixture prepared at the time of use (called "tank mix") of compositions separately comprising the various constituents or vehicles.

The compositions used in the invention can also contain any kind of other ingredients such as, for example, protective colloids, adhesives, thickening agents, thixotropic agents, penetrating agents, stabilizing agents, sequestering agents and the like. More generally, these compositions can be combined with all the solid or liquid additives corresponding to the conventional formulating techniques.

Generally, the compositions according to the invention usually contain from 0.00001 to 95% of active material(s) of formula (I), preferably 0.5 to 90% for the concentrated compositions.

Except when otherwise indicated, the percentages given in the present account are percentages by weight.

In the present account, the term "vehicle" denotes a natural or synthetic, organic or inorganic material with which the active material(s) is combined to facilitate its application to the parts of the plant. This vehicle is thus generally inert and it must be acceptable in agriculture and/or in aviculture and/or in the veterinary field and/or, preferably, in the field of animal rearing. The vehicle can be solid (clays, natural or synthetic silicates, silica, resins, waxes, solid fertilizers and the like) or liquid (water, alcohols, especially butanol, and the like).

The surface-active agent can be an emulsifying, dispersing or wetting agent of ionic or nonionic type or a mixture of such surface-active agents. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols (especially alkylphenols or arylphenols), salts of esters of sulphosuccinic acids, taurine derivatives (especially alkyltaurates), phosphoric esters of polyoxyethylenated phenols or alcohols, esters of fatty acids and of polyols, and the derivatives of the above compounds containing sulphate, sulphonate and phosphate functional groups. The presence of at least one surface-active agent is generally indispensable when the active material(s) and/or the inert vehicle is/are not soluble in water and when the carrier agent for application is water.

The surface-active agent content of the compositions according to the invention is advantageously between 2% and 40%.

The compositions according to the invention can be in fairly diverse, solid or liquid forms.

There may be mentioned, as forms of solid compositions, powders for dusting, wettable powders (or powder to be sprayed with water) and granules, in particular water-dispersible granules.

Wettable powders (or powder to be sprayed) generally contain 1 to 90% of active material(s), as well as, in addition to the solid vehicle, from 1 to 30% of a wetting agent, from 2 to 20% of a dispersing agent and, when this is necessary, from 0.1 to 10% of one or more stabilizing agents and/or other additives, such as penetrating agents, adhesives, or anticlumping agents, dyes, and the like.

To obtain powders to be sprayed or wettable powders, the active materials are intimately mixed, in suitable mixers, with the additional substances and the mixture is milled with mills or other suitable grinders. Powders to be sprayed are thereby obtained with advantageous wettability and suspensibility; they can be suspended in water at any desired concentration and these suspensions can be used very advantageously, in particular for application, for example, to litter.

Various compositions of wettable powders (or powders to be sprayed) are given here as examples:

WP Example 1

| | |
|---|---|
| active material(s) | 50% |
| ethoxylated fatty alcohol (wetting agent) | 2.5% |
| ethoxylated phenylethylphenol (dispersing agent) | 5% |
| chalk (inert vehicle) | 42.5% |
| WP Example 2: | |
| active material(s) | 10% |
| C13 branched-type synthetic oxo alcohol, ethoxylated with 8 to 10 molecules of ethylene oxide (wetting agent) | 0.75% |
| neutral calcium lignosulphonate (dispersing agent) | 12% |
| calcium carbonate (inert filler) | q.s. for 100% |

WP Example 3

This wettable powder contains the same ingredients as in the above example, in the proportions below:

| | |
|---|---|
| active material(s) | 75% |
| wetting agent | 1.50% |
| dispersing agent | 8% |
| calcium carbonate (inert filler) | q.s. for 100% |

WP Example 4

| | |
|---|---|
| active material(s) | 90% |
| ethoxylated fatty alcohol (wetting agent) | 4% |
| ethoxylated phenylethylphenol (dispersing agent) | 6% |

WP Example 5

| | |
|---|---|
| active material(s) | 50% |
| mixture of anionic and nonionic surface-active agents (wetting agent) | 2.5% |
| sodium lignosulphonate (dispersing agent) | 5% |
| kaolin clay (inert vehicle) | 42.5% |

Aqueous dispersions and emulsions, for example the compositions obtained by diluting a wettable powder according to the invention with water, come within the general scope of the present invention. Emulsions can be of the water-in-oil or oil-in-water type and they can have a thick consistency, like that of a "mayonnaise".

The compositions according to the invention can be formulated in the form of granules, in particular of water-dispersible granules.

The granules can be obtained by extrusion, by compacting, by impregnation of a granulated vehicle or by granulation from a powder (the active material content in these granules being between 0.5 and 85% for the latter cases).

The water-dispersible granules, with a bulk density generally of between approximately 0.2 and 0.8 (preferably 0.3 to 0.6), have a particle size generally of between approximately 0.1 and 3 mm and preferably between 0.3 and 1.5 mm.

The active material content of these granules is generally between approximately 1% and 90%, and preferably between 25% and 85%.

The remainder of the granule is essentially composed of a solid filler and, optionally, of surface-active adjuvants which confer water-dispersibility properties on the granule. These granules can be essentially of two distinct types according to whether the filler used is soluble or insoluble in water. The filler can be inorganic or organic. Excellent results were obtained with urea. Kaolin or bentonite can also be used. The granules advantageously comprise surface-active agents (in a proportion of 2 to 20% by weight of the granule), of which more than half consists of, for example, at least one dispersing agent, essentially anionic, such as an alkali metal or alkaline-earth metal polynaphthalenesulphonate or an alkali metal or alkaline-earth metal lignosulphonate, the remainder consisting of nonionic or anionic wetting agents such as an alkali metal or alkaline-earth metal alkylnaphthalenesulphonate.

Moreover, although this is not indispensable, it is possible to add other adjuvants such as antifoaming agents.

The granule according to the invention can be prepared by mixing the necessary ingredients and then granulating according to several techniques known per se (granulator, fluid bed, atomizer, extrusion, and the like). The preparation generally finishes with a crushing followed by a sieving to the particle size chosen within the limits mentioned above. It is also possible to use granules obtained as above and then impregnated with a composition containing the active material(s).

It is preferably obtained by extrusion, by carrying out the preparation as indicated in the examples below.

DG Example 1: Dispersible Granules

90% by weight of active material(s) and 10% of urea in the form of pearls are mixed in a mixer. The mixture is then milled in a pin mill. A powder is obtained which is moistened with approximately 8% by weight of water. The moist powder is extruded in a perforated-roller extruder. A granule is obtained which is dried, and then crushed and sieved, so as to retain respectively only the granules having a size of between 0.15 and 2 mm.

DG Example 2: Dispersible Granules

The following constituents are mixed in a mixer:

| | |
|---|---|
| active material(s) | 75% |
| wetting agent (sodium alkylnaphthalene-sulphonate) | 2% |
| dispersing agent (sodium polynaphthalene-sulphonate) | 8% |
| water-insoluble inert filler (kaolin) | 15% |

This mixture is granulated on a fluid bed in the presence of water and then dried, crushed and sieved go as to obtain granules having a size of between 0.15 and 0.80 mm.

DG Example 3: Dispersible Granules

The following constituents are mixed in a mixer:

| | |
|---|---|
| active material(s) | 80% |
| wetting agent (dioctyl sodium sulphosuccinate) | 2% |
| dispersing agent (sodium polycarboxylate) | 5% |
| antifoaming agent (silicone oil) | 0.3% |
| alkaline lignosulphonate | 2.7% |

This mixture is granulated on a fluid bed in the presence of water and then dried, crushed and sieved so as to obtain granules having a size of between 0.15 and 0.80 mm.

These granules can be used alone or in solution or dispersion in water so as to obtain the required dose. They can also be used to prepare combinations with other active materials, the latter being in the form of wettable powders, or of aqueous suspensions or granules.

There may be mentioned, as forms of liquid compositions or those intended to constitute liquid compositions at the time of application, solutions, in particular water-soluble concentrates, emulsions, emulsifiable concentrates or suspension concentrates, which can be suspoemulsions (suspensions of a solid in a liquid emulsion).

The suspension concentrates, applicable by spraying, are prepared so as to obtain a stable fluid product which does not settle out and they generally contain from 5 to 75% of active material(s), from 0.5 to 25% of surface-active agents, from 0.1 to 10% of thixotropic agents and from 0 to 10% of suitable additives, such as antifoaming agents, corrosion inhibitors, stabilizing agents, penetrating agents and adhesives and, as vehicle, water and/or an organic liquid in which the active material(s) is/are insoluble or nearly insoluble: certain organic solid materials or inorganic salts can be dissolved in the vehicle to aid in preventing sedimentation or as antigels for water.

These suspension concentrates used in the invention preferentially comprise 10 to 35% of active material of formula (I), 20 to 40% of water, 20 to 40% of vegetable oil and 2 to 20% of surface-active, wetting or dispersing agents, in particular salts and esters of ethoxylated polystyrylphenols and ethoxylated alkylphenols.

A suspension concentrate composition is given here as an example:

| | |
|---|---|
| active material(s) | 500 g |
| polyethoxylated tristyrylphenyl phosphate | 50 g |
| polyethoxylated alkylphenol | 50 g |
| sodium polycarboxylate | 20 g |
| ethylene glycol | 50 g |
| organopolysiloxane oil (antifoaming agent) | 1 g |
| polysaccharide | 1.5 g |
| water | 316.5 g |

| | |
|---|---|
| active material(s) | 200 g |
| polyethoxylated tristyrylphenyl phosphate | 100 g |
| polyethoxylated alkylphenol | 79 g |
| sodium polycarboxylate | 20 g |
| organopolysiloxane oil (antifoaming agent) | 1 g |
| water | 300 g |
| sunflower or soya oil | 300 g |

The invention also relates to the method of application of the compositions described above. For the process for the treatment of floors, litter and liquid manure, it is preferable to use granules, in particular water-dispersible granules. For non-horizontal sites, in particular the parts of buildings other than the floors, it is preferable to spray dilute liquid formulations, which can be obtained from solid or liquid concentrated compositions, preferably by dilution with water.

As regards the application of solid formulations in particular of granules, to floors, litter or liquid manure. It is possible to use several tens of grams of the composition for treating an animal rearing site with an area of 2000 m$^2$, in particular between 0.5 and 5 g per 100 m$^2$, depending on the concentration of compound (I) in the granules.

It is preferable to dissolve or disperse the granules in a suitable volume of water in order to treat the places, which can advantageously be done by spraying.

In accordance with this embodiment, it is also possible, after having spread the granules over the floor, to moisten the latter.

In the present application, when speaking of dissolving the granules in water, this must, of course, be understood as the dissolution of the excipient which forms the granules, the compound (I) then becoming dispersed in this water.

According to a second preferred embodiment of the invention, use is made of a suspension obtained by diluting a suspension concentrate or an emulsified concentrate of compound (I) in a given volume of water. The amount of compound of formula (I) applied is generally between 0.05 and 100 mg per m$^2$, in particular preferably between 0.5 and 50 mg/m$^2$ and more preferentially still between 10 and 15 mg/m$^2$.

Generally, the volume of composition applied per m$^2$ can be between 0.1 and 1 liter.

Generally, the application of the compositions according to the invention is preferably carried out in the absence of animals.

The invention is applied not only in the treatment of litter and liquid manure associated with small animals in intensive rearing but also in the rearing of large animals, in particular cattle, and in all cases of grouping together animals, in particular animals for rearing. Mention may be made, for example, of the "feed lot" of North America, which is an open-air grouping together of a large number of cattle (for example 1000 to 20,000) over a period of 1 to several months before slaughter.

Another subject of the invention is a process for combating darkling beetles according to the characteristics described above relating to the process for the treatment of the various sites (floors, litter, liquid manure, places or buildings).

A further subject of the invention is a ready-to-use litter or a litter with litter components which are capable of being obtained by the process according to the invention. In other words, the invention also relates to such products comprising at least one compound according to the invention. in particular at a dose of 0.01 to 50 mg/kg of ready-to-use litter, preferably of 0.1 to 10 mg/kg.

According to another aspect of the present invention, the latter relates to pesticidal compositions, especially insecticidal compositions, comprising an active compound of formula (I) [preferably the compound (A)] as a mixture with carbaryl, this mixture optionally additionally comprising the various other formulation components as described above for the compositions comprising only the compound of formula (I) as active material.

The compositions comprising two active materials, one of formula (I) and the other being carbaryl, are particularly advantageous due to their broad spectrum with respect to all kinds of pests or parasites, in addition to darkling beetles, in particular spiders, ants, flies, ticks and white grubs (cockchafer grubs), as well as due to their speed of action (shock effect) and their persistence. These compositions with two active materials are particularly effective and inexpensive in their application.

These compositions provide an unexpected synergistic effect which potentiates the activity ranges of both a compound of formula (I) and carbaryl. The compositions achieve a high degree of pest control where the individual active materials are substantially inactive at low concentrations. This feature permits on the one hand a broadening of the activity spectrum against pests and on the other hand an enhancement of safety of application.

These compositions containing two active materials (of formula (I)+carbaryl), when they are concentrated compositions, generally comprise a) 0.000001% to 10% of active material of formula (I) preferably 0.00001% to 10%, more preferably 0.0001 to 0.001%, and b) 0.0005 to 95% of carbaryl, preferably 0.5 to 90%, more preferably 1 to 50%. The solid formulations generally comprise from 0.5 to 60% of carbaryl. The liquid formulations generally comprise from 5 to 90% of carbaryl, preferably 40 to 80%. For applications in private houses and gardens, the carbaryl content is generally between 1 and 20%, preferably from 2 to 8%; for applications by professionals, the content is generally between 10 and 50%.

The compound of formula (I)/carbaryl ratio by weight is generally between 0.005 and 0.5, preferably between 0.01 and 0.1.

These two-constituent compositions are also particularly useful in treating lawns, gardens, private houses and various buildings.

The description of the invention will now be described in more detail. In its application, using embodiments intended to illustrate the invention in a non-limiting way and to show how it can be implemented.

EXAMPLE 1

A poultry house was treated with water-dispersible granules containing 80% of compound (A) at the rate of 150 g/ha=1.5 g/100 m$^2$. The treatment took place on the clean litter before the poultry was installed therein. The clean litter was essentially composed of straw.

On the day after the treatment, a group of chicks aged 1 to 2 days was installed in the rearing house at the rate of approximately 7 animals per m$^2$.

The change in the population of darkling beetles (*Alphitobius diaperinus*) in the litter was regularly monitored using 9 homogeneously distributed traps. Measurements were carried out each week from the second week after the treatment until rearing was halted.

The total population of darkling beetles in the 9 traps of the treated poultry house varied between 11 and 96 until the 9th week after treatment whereas, in a similar but untreated poultry house, the population of darkling beetles (larvae and adults) oscillated between 1000 and 3000 at each counting point.

A mean control (or degree of destruction of the darkling beetles) of 95 to 97% was thus obtained according to the invention, with a control of 86% during the 10th week (end of a rearing cycle).

EXAMPLE 2

A 5 milliliter liquid mixture comprises the compound (A) and carbaryl, as well as water and acetone. This mixture is poured onto 40 g of wheat flour. The water/acetone ratio by volume is equal to 9/1. The amount of active material is such that there is a concentration of 0.4 ppm=0.00004% for the compound (A) and 100 ppm=0.0001% for the carbaryl.

10 adult *Tenebrio molitor* insects are placed in a flask containing the treated flour. The insects are observed to have a mortality of 100%.

EXAMPLE 3

An application was carried out at the surface of poultry dung and of cow dung treated beforehand with fly larvae. At a dose of 25 ppm of compound (A), larval development of the flies was completely inhibited (100% effectiveness with respect to untreated controls).

EXAMPLE 4

Receptacles containing a floor, poultry litter and poultry dung were treated with compound (A). These substrates were infested with larvae of the house fly and of the darkling beetle (*Alphitobius diaperinus*).

Treatments were carried out with doses of 1, 10 and 100 ppm administered on a single occasion using compositions of emulsion type or of granule type. 100% inhibition of the development of the larval stages (fly or darkling beetle) was observed for doses of 10 and 100 ppm, 99 to 100% inhibition of the development of the larval stages (fly or darkling beetle) was observed for the dose of 1 ppm.

EXAMPLE 5

Ten (10) gram pieces of potato were placed into individual jars. Carbaryl and compound (A) and combinations thereof, as shown below in Tables I and II, were substantially dissolved in a mixture of water:acetone-surfactant solution; DMF in a ratio of 90:9:1. The acetone-surfactant solution comprised acetone. Triton® 152, and Triton® 172 mixed in volumetric ratio of about 785:1:3. Two (2) mL aliquots of solution were added to 10 gm potato pieces and the treated potato pieces were dried overnight to provide concentrations of active materials in parts per million according to Table I and II. Adult *Tenebrio molitor* and a strip of paper towel 1 cm by 3 cm were added to each jar. Mortality was rated at 1 day after treatment.

A synergistic effect is obtained whenever the activity of the combination of the compound of formula (I) with carbaryl is greater than the sum of the activities of the individually applied compounds.

For example, the expected pesticidal activity We of a given combination of two pesticides can be calculated as follows (q.v. Colby, S. R., "Calculating synergistic and antagonistic response of herbicide combinations". Weeds 15, 1967 pp. 20–22): We=X+[Y·(100−x)]/100 wherein X is the percentage mortality, compared with untreated controls, after treatment with compound (A) at a rate p in parts per million; and Y is the percentage mortality, compared with untreated controls, after treatment by carbaryl at rate q in parts per million; and We is thus the expected mortality after treatment with compound (A) and carbaryl at a rate of application of p+q ppm. If the actually observed value is greater than the expected value We then there is synergism.

TABLE I

Individual Materials

| Rate Compound (A) (ppm) | % Mortality | Rate Carbaryl (ppm) | % Mortality |
|---|---|---|---|
| 2 | 100 | 400 | 93 |
| 0.5 | 87 | 100 | 80 |
| 0.125 | 7 | 25 | 27 |
| 0.03 | 0 | 6.25 | 0 |

TABLE II

Combinations

| Rates of Compound (A), Carbaryl (ppm) | Expected % Mortality | Actual % Mortality |
|---|---|---|
| 0.125, 25 | 32 | 87 |
| 0.125, 6.25 | 7 | 80 |
| 0.03, 25 | 27 | 53 |
| 0.03, 6.25 | 0 | 13 |

What is claimed is:

1. A process for the antiparasitic treatment of a site infested by darkling beetles, said process comprising applying to said site, in an amount effective to control said darkling beetles, a composition comprising a compound having the formula (I)

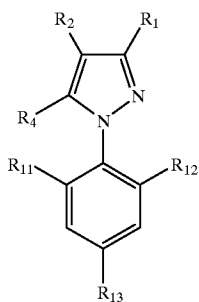

(I)

wherein
- $R_1$ is halogen, CN or methyl;
- $R_2$ is $S(O)_n R_3$ or haloalkyl;
- $R_3$ is alkyl or haloalkyl;
- $R_4$ is hydrogen, halogen, $NR_5R_6$, $S(O)_m R_7$, $C(O)R_7$, $C(O)O$—$R_7$, alkyl, haloalkyl, $OR_8$ or —$N=C(R_9)(R_{10})$;
- $R_5$ and $R_6$ are, independently, hydrogen, alkyl, haloalkyl, $C(O)$alkyl, alkoxycarbonyl or $S(O)_r CF_3$;
- $R_7$ is alkyl or haloalkyl;
- $R_8$ is alkyl, haloalkyl or hydrogen;
- $R_9$ is alkyl or hydrogen;
- $R_{10}$ is phenyl optionally substituted by one or a number of halogen atoms or groups selected from OH, —O-alkyl, —S-alkyl, cyano and alkyl;
- $R_{11}$ and $R_{12}$ are, independently, hydrogen, halogen, CN or $NO_2$;
- $R_{13}$ is halogen, haloalkyl, haloalkoxy, $S(O)_q CF_3$ or $SF_5$;
- m, n, q and r are, independently, an integer 0, 1 or 2;

and at least one member selected from the group consisting of an agriculturally, aviculturally or veterinarily acceptable solid or liquid vehicle and an agriculturally, aviculturally or veterinarily acceptable surface-active agent.

2. The process according to claim 1, wherein the compound of formula (I) has at least one substituent selected from the group consisting of: (a) $R_1$ is CN; (b) $R_3$ is haloalkyl; (c) $R_4$ is $NH_2$; (d) $R_{11}$ and $R_{12}$ are, independently, a halogen atom; and (e) $R_{13}$ is haloalkyl.

3. The process according to claim 1, said site comprising the surroundings of animals.

4. The process according to claim 1, said site comprising a floor, litter, liquid manure, place, building, or building for commercial rearing.

5. The process according to claim 1, said site comprising a floor, litter, liquid manure, place, building, or building for commercial rearing intended to receive poultry.

6. The process according to claim 1, wherein said darkling beetle is *Alphitobius diaperinus*.

7. The process according to claim 1, wherein said darkling beetle is *Dermestes maculatus, Tenebrio molitor*, or a darkling beetle from the Tenebrionidae family.

8. The process according to claim 1, wherein said treatment is performed less than once per month.

9. The process according to claim 1, wherein said treatment is performed not more than once per rearing cycle.

10. The process according to claim 1, comprising applying to said site a composition comprising a compound of formula (I), said compound being present in an amount of from 0.00001 to 95% of said composition.

11. The process according to claim 1, comprising applying to said site a composition comprising a compound of formula (I), said compound being present in an amount of between 2 and 40% of said composition.

12. The process according to claim 1, where said composition is a dispersible granule, a suspension, or an emulsifiable concentrate.

13. The process according to claim 1, wherein said composition is a dispersible granule with a density of between 0.2 and 0.8 and a size of between 0.1 and 3 mm.

14. The process according to claim 1, wherein said composition is applied at a concentration of 0.05 mg/m² to 100 mg/m².

15. The process according to claim 1, wherein said treatment occurs in the absence of animals.

16. The process according to claim 1, wherein said composition is a ready-to-use litter comprising 0.01 to 50 mg of a compound of formula (I) per kg of ready-to-use litter.

17. The process according to claim 1, comprising applying to said site a composition comprising a compound of formula (I), said compound being present in an amount of from 0.5 to 90% of said composition.

18. The process according to claim 1, wherein said composition is a dispersible granule with a density of between 0.3 and 0.6 and a size of between 0.3 and 1.5 mm.

19. The process according to claim 1, wherein said composition is applied at a concentration of 0.5 mg/m² to 50 mg/m².

20. The process according to claim 1, wherein said composition is applied at a concentration of 10 mg/m² to 15 mg/m².

21. The process according to claim 1, wherein said composition is a ready-to-use litter, comprising 0.1 to 10 mg of a compound of formula (I) per kg of ready-to-use litter.

22. A process for the antiparasitic treatment of a site infested or capable of being infested by darkling beetles, said process comprising applying to said site, in an amount effective to control said darkling beetles, a composition comprising the compound 5-amino-3-cyano-1-(2,6-dichloro-4-trifluoromethylphenyl)-4-trifluoromethylsulfinylpyrazole and at least one member selected from the group consisting of an agriculturally, aviculturally, or veterinarily acceptable solid or liquid vehicle and an agriculturally, aviculturally, or veterinarily acceptable surface-active agent, wherein said composition is applied at a concentration of 0.5 mg/m² to 50 mg/m² and wherein said treatment is performed less than once per month.

23. The process according to claim 22, wherein said composition is applied at a concentration of 10 mg/m² to 15 mg/m².

24. A process for the antiparasitic treatment of a site infested or capable of being infested by darkling beetles, said process comprising applying to said site, in an amount effective to control darkling beetles, a composition comprising the compound 5-amino-3-cyano-1-(2,6-dichloro-4-trifluoromethylphenyl)-4-trifluoromethylsulfinylpyrazole and at least one member selected from the group consisting of an agriculturally, aviculturally or veterinarily acceptable solid or liquid vehicle and an agriculturally, aviculturally, or veterinarily acceptable surface-active agent, wherein said composition is applied at a concentration of 0.5 mg/m² to 50 mg/m², wherein said site is a site for commercial rearing of animals and wherein said treatment is performed not more than once per rearing cycle.

25. The process according to claim 24, wherein said composition is applied at a concentration of 10 mg/m² to 15 mg/m².

26. The process according to claim 24, wherein said site is a site for commercial rearing of poultry.

27. A process for the antiparasitic treatment of a site infested or capable of being infested by darkling beetles, said process comprising applying to said site, in an amount effective to control darkling beetles, a composition comprising the compound 5-amino-3-cyano-1-(2,6-dichloro-4-trifluoromethylphenyl)-4-trifluoromethylsulfinylpyrazole and at least one member selected from the group consisting of an agriculturally, aviculturally or veterinarily acceptable solid or liquid vehicle and an agriculturally, aviculturally or veterinarily acceptable surface-active agent, wherein said composition is a ready-to-use litter comprising 0.01 to 50 mg of said compound per kg of ready-to-use litter, and wherein said treatment is performed less than once per month.

28. The process according to claim 27, wherein said litter comprises 0.1 to 10 mg of said compound per kg of litter.

29. A process for the antiparasitic treatment of a site infested or capable of being infested by darkling beetles, said process comprising applying to said site, in an amount effective to control darkling beetles, a composition comprising the compound 5-amino-3-cyano-1-(2,6-dichloro-4-trifluoromethylphenyl)-4-trifluoromethylsulfinylpyrazole and at least one member selected from the group consisting of an agriculturally, aviculturally, or veterinarily acceptable surface-active agent, wherein said composition is a ready-to-use litter comprising 0.01 to 50 mg of said compound per kg of ready-to-use litter, wherein said site is a site for commercial rearing of animals and wherein said treatment is performed not more than once per rearing cycle.

30. The process according to claim 29, wherein said litter comprises 0.1 to 10 mg of said compound per kg of litter.

31. The process according to claim 29, wherein said site is a site for commercial rearing of poultry.

* * * * *